US011849967B2

(12) United States Patent
Tarunaga

(10) Patent No.: US 11,849,967 B2
(45) Date of Patent: Dec. 26, 2023

(54) SCORING DEVICE AND TREATMENT METHOD

(71) Applicant: TERUMO KABUSHIKI KAISHA, Tokyo (JP)

(72) Inventor: Akihiko Tarunaga, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 377 days.

(21) Appl. No.: 16/803,365

(22) Filed: Feb. 27, 2020

(65) Prior Publication Data

US 2020/0305926 A1 Oct. 1, 2020

(51) Int. Cl.
*A61B 17/3207* (2006.01)
*A61B 17/22* (2006.01)
*A61B 17/00* (2006.01)
*A61B 90/00* (2016.01)

(52) U.S. Cl.
CPC ........... *A61B 17/320725* (2013.01); *A61B 17/00234* (2013.01); *A61B 17/22* (2013.01); *A61B 90/08* (2016.02); *A61B 2017/00871* (2013.01); *A61B 2017/22002* (2013.01); *A61B 2017/22061* (2013.01); *A61B 2090/08021* (2016.02)

(58) Field of Classification Search
CPC .......... A61B 17/22; A61B 17/320725; A61M 25/104; A61M 2025/109
See application file for complete search history.

(56) References Cited

U.S. PATENT DOCUMENTS

| 5,196,024 A | * | 3/1993 | Barath | A61B 17/320725 606/191 |
|---|---|---|---|---|
| 7,338,463 B2 | | 3/2008 | Vigil | |
| 2005/0137617 A1 | * | 6/2005 | Kelley | A61B 17/320725 604/103.14 |
| 2008/0077165 A1 | * | 3/2008 | Murphy | A61B 17/320725 604/103.05 |
| 2012/0022563 A1 | * | 1/2012 | Leffel | A61M 25/104 606/159 |
| 2015/0250489 A1 | * | 9/2015 | Shimizu | A61B 17/32002 606/170 |

* cited by examiner

*Primary Examiner* — Ashley L Fishback
(74) *Attorney, Agent, or Firm* — Buchanan Ingersoll & Rooney PC

(57) ABSTRACT

A scoring device includes an elongate shaft, a balloon disposed on a far side of the shaft and inflatable radially of the shaft by a fluid flowing into the balloon, at least one storage tube disposed along an outer surface of the balloon and having a storage lumen defined therein, and an elongate scoring wire storable in the storage tube and made of a harder material than the balloon. The storage tube is fixed to the balloon or the shaft, and an opening portion is defined in the storage tube to provide fluid communication between outer and inner circumferential surfaces of the storage tube along the storage lumen when the balloon is inflated. The scoring wire is movable in the storage lumen along a longitudinal axis of the storage tube.

3 Claims, 6 Drawing Sheets

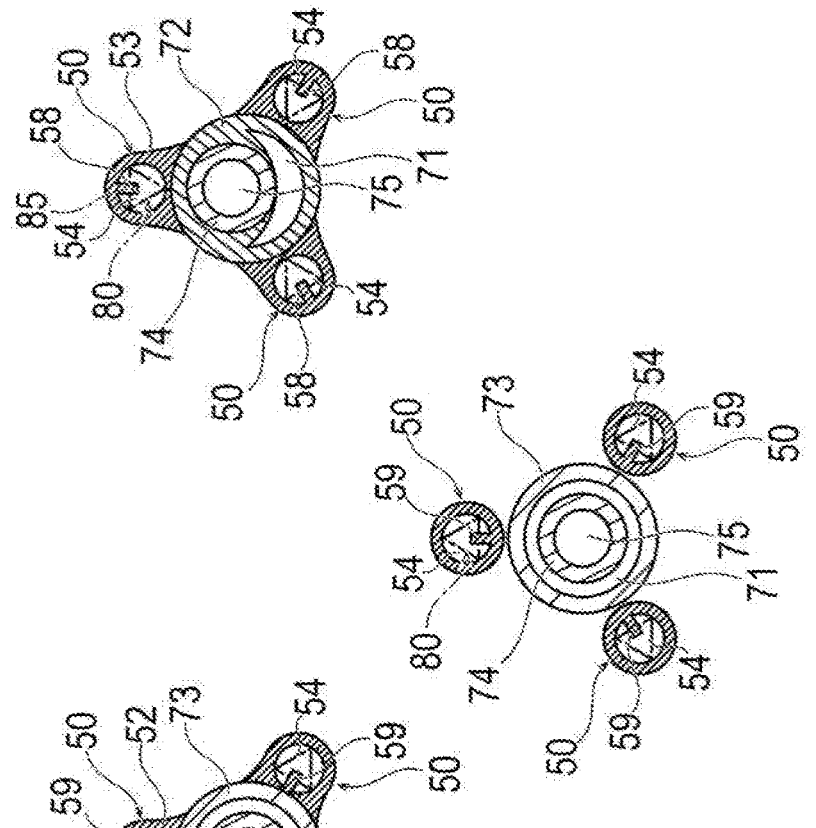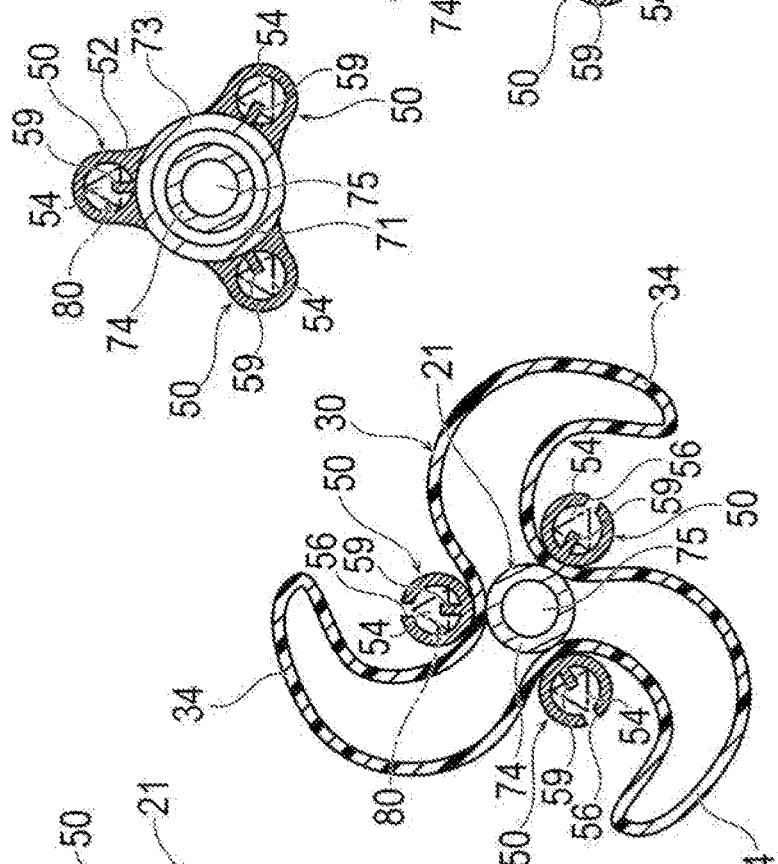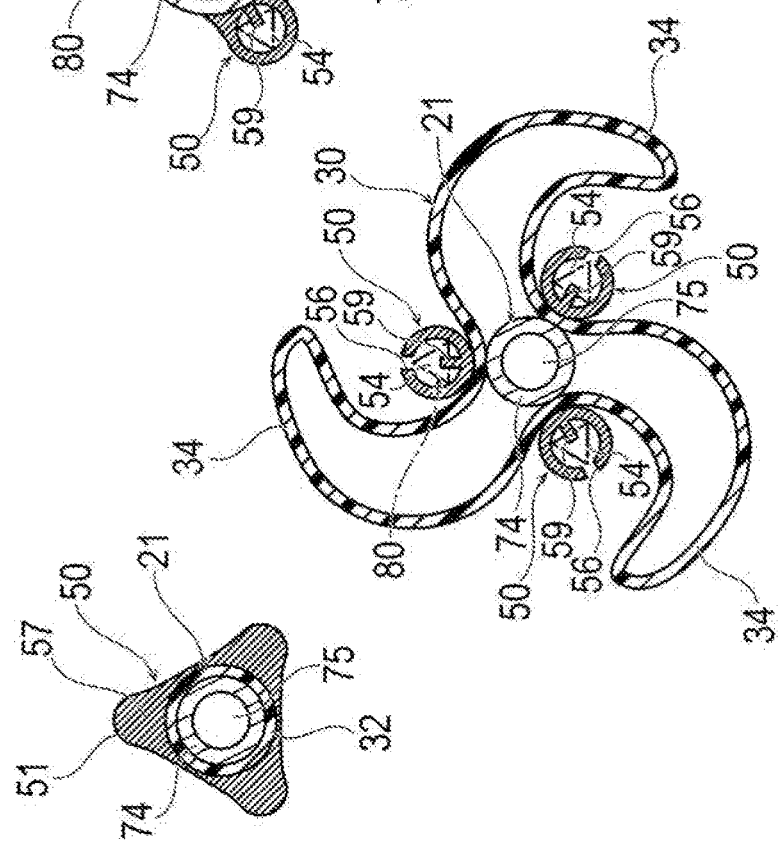

FIG. 4A
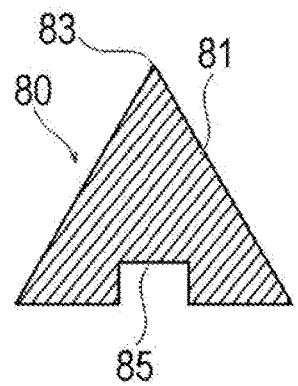
FIG. 4B
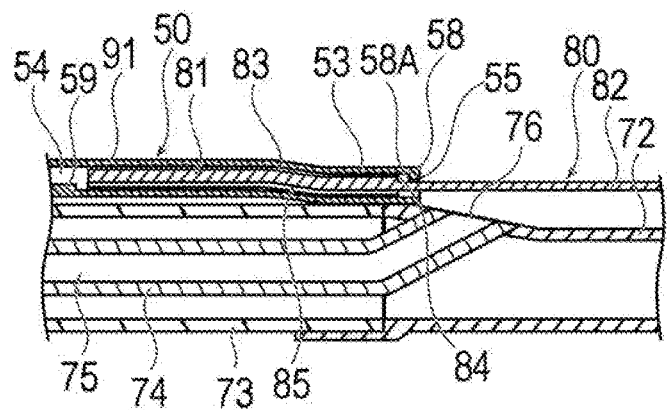
FIG. 5
FIG. 6A
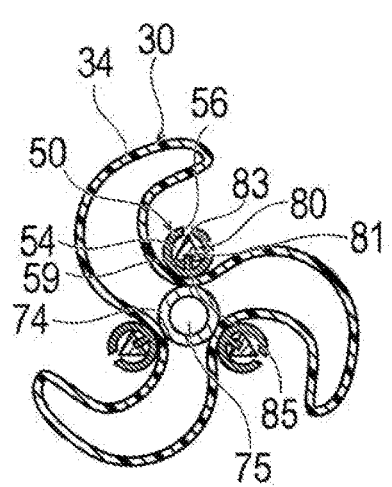
FIG. 6B
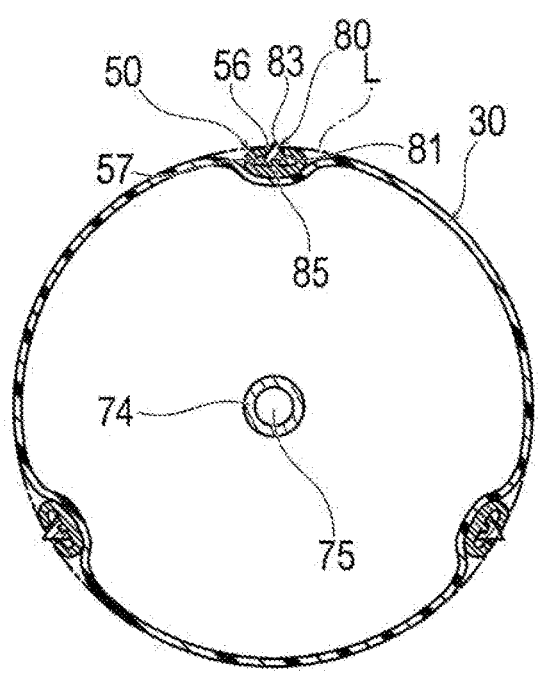

FIG. 9A
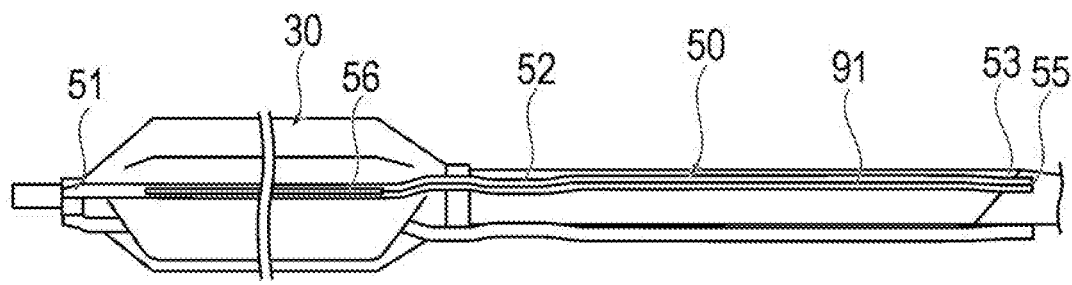
FIG. 9B
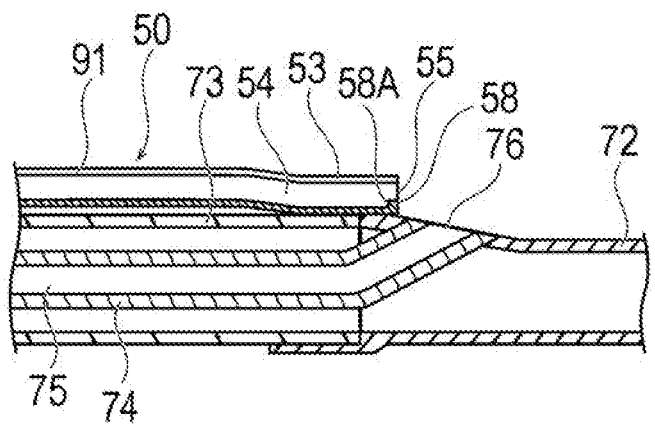
FIG. 10A
FIG. 10B
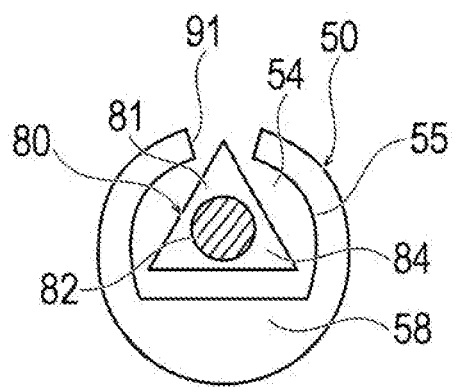 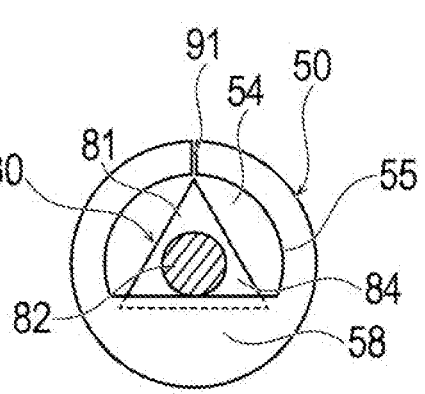

SCORING DEVICE AND TREATMENT METHOD

CROSS-REFERENCES TO RELATED APPLICATIONS

This application claims priority to Japanese Application No. 2019-058931 filed on Mar. 26, 2019, the entire content of which is incorporated herein by reference.

FIELD OF THE INVENTION

The present disclosure generally relates to a scoring device having scoring elements for fracturing a lesion area and a treatment method using such a scoring device.

BACKGROUND DISCUSSION

Percutaneous transluminal angioplasty has been practiced as a treatment for coronary artery disease or atherosclerosis. In percutaneous transluminal angioplasty, a balloon is used to physically dilate a coronary artery stenosis for securing a bloodstream. However, in the case of a heavily constricted stenosis caused by a calcified lesion area, the dilating pressure of a balloon is not enough to dilate the blood vessel properly. U.S. Pat. No. 7,338,463, for example, discloses a device in which hard blades are disposed on the surface of a balloon. The proposed device is capable of fracturing a lesion area in a blood vessel to dilate the blood vessel by pressing the blades against the lesion area under the dilating force from the balloon that is inflated.

In the device disclosed in U.S. Pat. No. 7,338,463, however, the balloon is rendered hard by the blades disposed thereon. The balloon is thus poor at its capabilities to pass through lesion areas and track a guide wire.

SUMMARY

Disclosed here are a scoring device and a treatment method that help a balloon improve its capabilities to pass through lesion areas and track a guide wire.

In accordance with an aspect of the present disclosure a scoring device includes an elongate shaft possessing a far-side and a near-side, a balloon disposed on the far-side of the shaft and inflatable radially of the shaft by a fluid introduced into the balloon, with the balloon possessing a near-side and a far-side at opposite ends of the balloon; at least one storage tube disposed along an outer surface of the balloon, and a storage lumen defined in the at least one storage tube; and an elongate scoring wire storable in the storage tube and made of a material harder than the balloon. The storage tube is fixed to the balloon or the shaft and includes an opening portion that provides fluid communication between outer and inner circumferential surfaces of the storage tube along the storage lumen when the balloon is inflated. The scoring wire is movable in the storage lumen along a longitudinal axis of the storage tube.

In accordance with an aspect of the disclosure here, a treatment method comprises inserting a balloon into a living body lumen until the balloon reaches a lesion area in the living body lumen, with the balloon including at least one storage tube on an outer surface of the balloon, inflating the balloon, deflating the balloon, placing an elongate scoring wire made of a material that is harder than the balloon in a portion of the storage tube that is on the outer surface of the balloon; inflating the balloon to apply an outwardly directed force to the scoring wire to cause the scoring wire to score at least a portion of the lesion area; and dilating the lesion area with the inflated balloon.

The scoring device thus constructed can be brought into a state in which the scoring wire is not disposed in at least a portion of the storage tube along the outer surface of the balloon. The balloon on which the scoring wire is not disposed is pliably bendable and tends to be small in diameter. Therefore, the scoring device has an improved ability to pass through a living body lumen to a lesion area and to track a guide wire.

The treatment method arranged as described above is able to try to dilate a lesion area using the balloon that is pliable and small in diameter with no scoring wire disposed thereon. In a case where the lesion area cannot be dilated by the balloon alone, the treatment method uses the scoring wire to fracture the lesion area while dilating the lesion area.

In accordance with another aspect, a scoring device configured to score a lesion in a lumen in a living body comprises an elongate shaft possessing a far-side and a near-side, a longitudinally extending inflatable balloon disposed on the far-side of the shaft, and a lumen in communication with an interior of the balloon to introduce fluid into the interior of the balloon to inflate the balloon radially outwardly, with the balloon possessing a near-side and a far-side at opposite ends of the balloon, and a longitudinally extending storage tube disposed on the outer surface of the balloon and extending along a longitudinal extent of the balloon so that inflation of the balloon causes the storage tube to move radially outwardly. The storage tube possesses a near-side end that is open and that communicates with a storage lumen extending toward a far-side of the storage tube. The storage tube is fixed relative to the balloon in a far-side direction and near-side direction, with inflation of the balloon causing the storage tube to move outwardly away from the shaft. An elongate scoring wire is configured to be introduced into the storage lumen by way of the open near-side end and moved along the storage lumen in the far-side direction. The elongate scoring wire includes a manipulating wire and a scoring element, wherein the scoring element is fixed to a far-side end of the manipulating wire so that movement of the manipulating wire by an operator moves the scoring element. The scoring element possesses a greater hardness than the balloon. The storage tube includes an opening portion through which the scoring element passes when the balloon is inflated and the storage tube moves radially outwardly so that the scoring element is positioned to score the lesion in the lumen of the living body, wherein the opening portion provides fluid communication between outer and inner circumferential surfaces of the storage tube along the storage lumen when the balloon is inflated.

BRIEF DESCRIPTION OF THE DRAWINGS

FIG. 3A is a cross-sectional view of a catheter taken along the section line 3A-3A of FIG. 2;

FIG. 3B is a cross-sectional view of the catheter taken along the section line 3B-3B of FIG. 2;

FIG. 3C is a cross-sectional view of the catheter taken along the section line 3C-3C of FIG. 2;

FIG. 3D is a cross-sectional view of the catheter taken along the section line 3D-3D of FIG. 2;

FIG. 3E is a cross-sectional view of the catheter taken along the section line 3E-3E of FIG. 2;

FIG. 4A is a cross-sectional view of a scoring wire taken along the section line 4A-4A of FIG. 2;

FIG. 4B is a cross-sectional view of the scoring wire taken along the section line 4B-4B of FIG. 2;

FIG. 5 is a fragmentary longitudinal cross-sectional view illustrating the manner in which a scoring wire is inserted into a storage tube;

FIG. 6A is a transverse cross-sectional view illustrating the manner in which scoring wires are disposed in respective storage tubes along a balloon before the balloon is inflated;

FIG. 6B is a transverse cross-sectional view illustrating the manner in which the scoring wires are disposed in the respective storage tubes along the balloon that has been inflated;

FIG. 9A is a plan view of a scoring device according to a fourth modification;

FIG. 9B is a fragmentary longitudinal cross-sectional view of the scoring device according to the fourth modification;

FIG. 10A is a transverse cross-sectional view of a storage tube and a scoring wire according to the fourth modification, the view illustrating the manner in which the scoring element is being inserted into the storage tube; and FIG. 10B is a transverse cross-sectional view of the storage tube and the scoring wire according to the fourth modification, the view illustrating the manner in which the scoring element has been stored in the storage tube.

DETAILED DESCRIPTION

Figure 1:
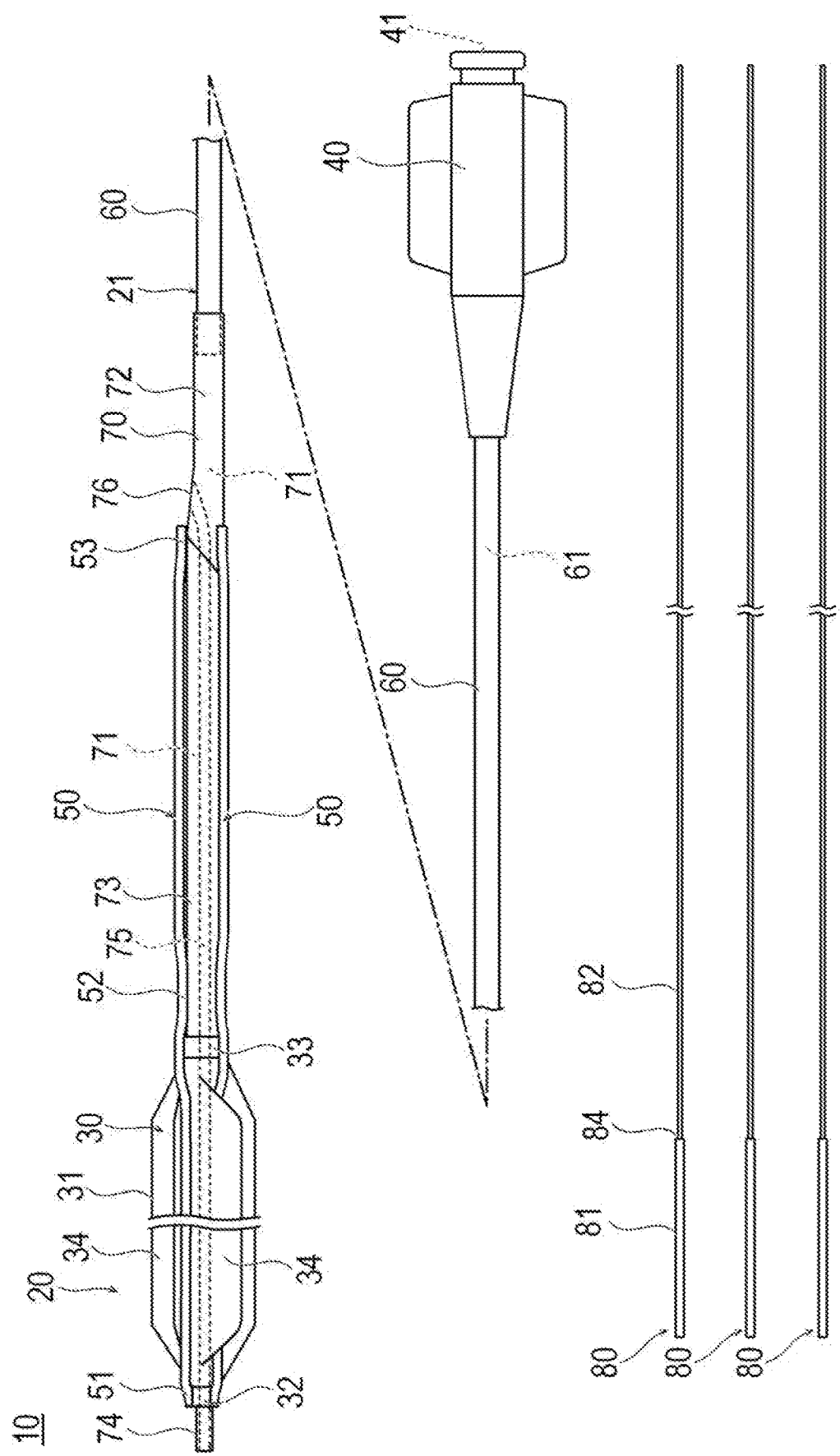
FIG. 1 is a plan view of a scoring device according to an embodiment of the present disclosure.

Set forth below with reference to the accompanying drawings is a detailed description of embodiments of scoring devices and treatment methods representing examples of the inventive scoring devices and treatment methods disclosed here. The dimensions or scales on the drawings may be exaggerated or different from actuality/reality for convenience of description and illustration. In the present description and drawings, components that have essentially identical functions are denoted by identical reference characters and a detailed description of such components is not repeated. In the present description, the side of a device that is to be inserted into a living body lumen is referred to as the "far side," whereas the surgeon side of the device that is to be manipulated is referred to as the "near side."

A scoring device 10 according to one embodiment disclosed by way of example is a device for dilating a calcified hard lesion area or stenosis, for example. In the present description, the side of a functionalized device that is to be inserted into a lumen shall be referred to as "far side," whereas the surgeon side of the device that is to be manipulated as "near side."

Figure 2:
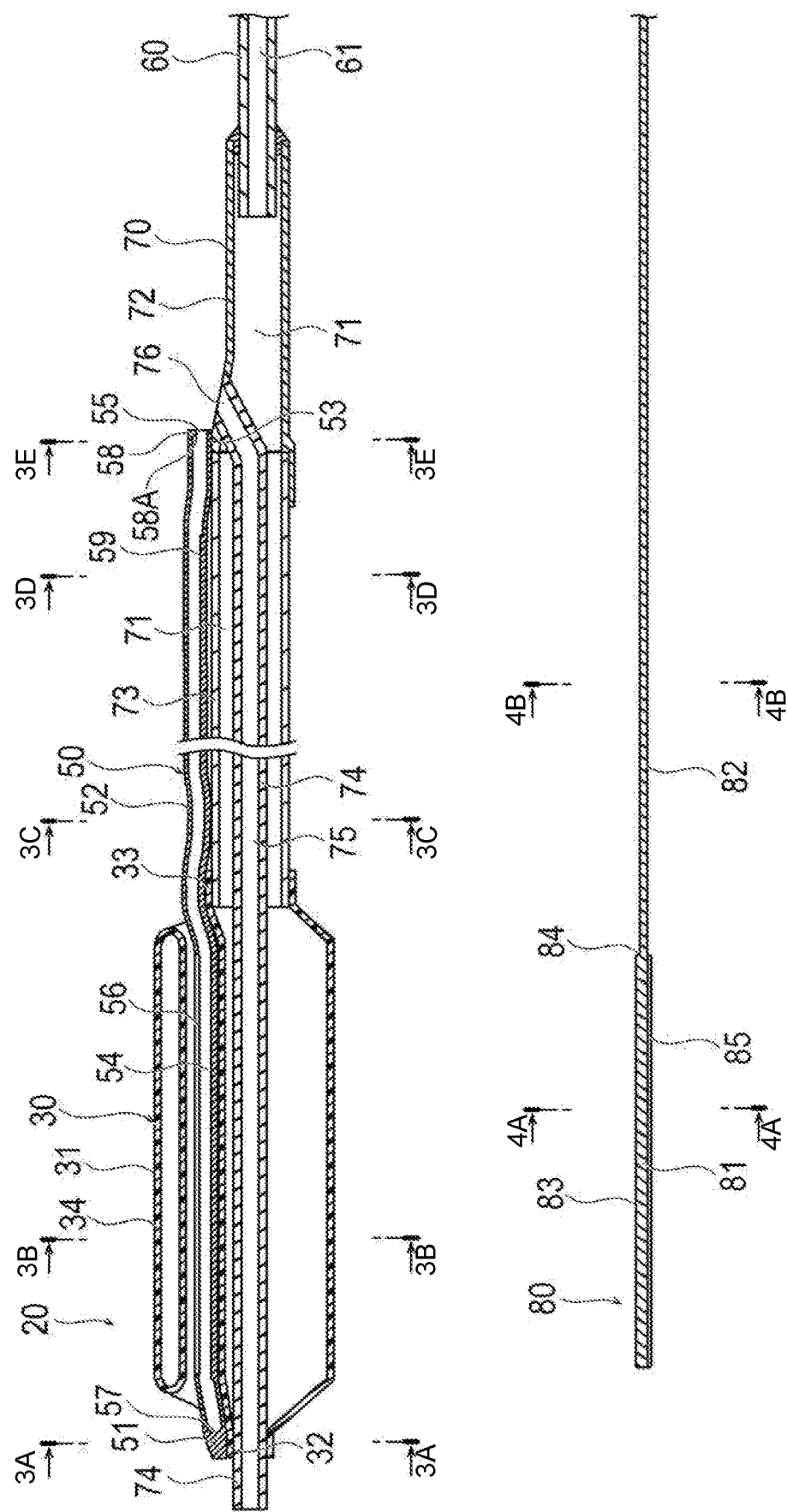
FIG. 2 is a longitudinal cross-sectional view of the scoring device according to the embodiment.

As illustrated in FIGS. 1 and 2, the scoring device 10 includes a catheter 20 and a plurality of scoring wires 80 that are insertable into the catheter 20.

The structure of the catheter 20 will first be described below. The catheter 20 may be a type of catheter called the rapid-exchange type catheter with a guide wire lumen disposed only in a far-side portion of the catheter. The catheter 20 includes an elongate shaft 21, a balloon 30 disposed on a distal end of the shaft 21, a hub 40 fixed to a proximal end of the shaft 21, and a plurality of storage tubes 50 for storing the scoring wires 80 inserted respectively into the storage tubes 50.

The shaft 21 includes a tubular near-side shaft 60 fixed to the hub 40 and a far-side shaft 70 fixed to a far-side portion of the near-side shaft 60. The far-side shaft 70 includes an outer tube 73, an intermediate shaft 72 fixed to a near-side portion of the outer tube 73, and an inner tube 74 disposed in the outer tube 73.

The outer tube 73 is a tubular body positioned in a far-side portion of the shaft 21. The outer tube 73 includes a far-side portion joined to a near-side portion of the balloon 30 so that a fluid-tight seal is maintained between the far-side portion of the outer tube 73 and the near side portion of the balloon 30. A first lumen 71 is defined in the outer tube 73. The first lumen 71 allows a fluid for inflating the balloon 30 to flow therein.

The intermediate shaft 72 is a tubular body positioned between the outer tube 73 and the near-side shaft 60. The intermediate shaft 72 has a far-side portion fixed to the near-side portion of the outer tube 73. The first lumen 71 is also defined in the intermediate shaft 72. The intermediate shaft 72 has a near-side portion fixed to the far-side portion of the near-side shaft 60.

The inner tube 74 is a tubular body extending coaxially through the outer tube 73 and the balloon 30. The inner tube 74 has a far-side portion extending in a far-side direction from the farthermost end of the balloon 30, and is joined to a far-side portion of the balloon 30 so that a liquid-tight seal is maintained between the far-side portion of the inner tube 74 and the far-side portion of the balloon 30. The inner tube 74 has a near-side portion extending through a side port defined in a side wall of the intermediate shaft 72 and fixed to the intermediate shaft 72 so that a fluid-tight seal is maintained between the near-side portion of the inner tube 74 and the intermediate shaft 72. The near-side portion of the inner tube 74 has an inner tube opening portion 76 defined therein that is exposed outside the intermediate shaft 72. The inner tube 74 has an inner space defined therein that extends from the far-side end of the inner tube 74 to the inner tube opening portion 76 as a second lumen 75 for receiving a guide wire inserted therein.

The material from which the outer tube 73, the inner tube 74, and the intermediate shaft 72 are fabricated is not limited to any particular materials, though they may be made of a polymeric material such as polyolefin (for example, polyethylene, polypropylene, polybutene, ethylene-propylene copolymer, ethylene-vinyl acetate copolymer, ionomer, a mixture of two or more of these polyolefins, or the like), cross-linked polyolefins, polyvinyl chloride, polyamide, polyamide elastomer, polyester, polyester elastomer, polyurethane, polyurethane elastomer, fluororesin, polyimide, or the like, a mixture of these polymeric materials, or may be a multi-layer tube of two or more of the above polymeric materials, or the like.

The balloon 30 is a member for dilating a lesion area in a living body lumen by inflating the balloon. The balloon 30, when inflated, can also press the scoring wires 80 against the lesion area. The balloon 30 has a substantially cylindrical tubular portion 31 having substantially the same diameter in an axially central region thereof. The balloon 30 also has, on a far side of the tubular portion 31, a balloon far-side fixed portion 32 joined to an outer surface of the inner tube 74 so that a fluid-tight seal is maintained between the far-side fixed portion 32 of the balloon and the outer surface of the inner tube 74. Furthermore, the balloon 30 has, on a near side of the tubular portion 31, a balloon near-side fixed portion 33 joined to an outer surface of the far-side portion of the outer tube 73 so that a fluid-tight seal is maintained between the balloon near-side fixed portion 33 and the outer surface of the far-side portion of the outer tube 73. The inside of the balloon 30 is held in fluid communication with the first lumen 71, so that an inflating fluid can flow through the first lumen 71 into the balloon 30 from the proximal end thereof. The balloon 30 is inflated when the inflating fluid flows into the balloon 30, and deflated when the inflating fluid that has flowed into the balloon 30 is discharged from the balloon.

As illustrated in FIGS. 2 and 3B, the balloon 30 includes a plurality of pleats 34 projecting radially outwardly. Each of the pleats 34 is folded back on itself in a radially outer area and shaped as a fold. The number of pleats 34 is not limited to any particular number, but should preferably be two or more. According to the present embodiment, the balloon 30 includes three pleats 34. The pleats 34 are spaced from each other at substantially equal intervals in the circumferential directions of the balloon 30. Each of the pleats 34 is bent into a shape coiled circumferentially around the inner tube 74. The pleats 34 may be loosely coiled around the inner tube 74 with gaps therebetween or may be tightly coiled around the inner tube 74 with almost no gaps therebetween. Alternatively, the balloon 30 may be free of the pleats 34.

The balloon 30 should preferably be made of a material that is flexible to a certain extent, e.g., polyolefin such as polyethylene, polypropylene, polybutene, ethylene-propylene copolymer, ethylene-vinyl acetate copolymer, ionomer, a mixture of two or more of these polyolefins, or the like, thermoplastic resin such as soft polyvinyl chloride resin, polyamide, polyamide elastomer, polyester, polyester elastomer, polyurethane, fluororesin, or the like, silicone rubber, latex rubber, or the like.

As illustrated in FIGS. 1 through 3E, the near-side shaft 60 is tubular in shape and has a near-side lumen 61 defined therein. The near-side lumen 61 is kept in fluid communication with the first lumen 71. The near-side lumen 61 allows the fluid for inflating the balloon 30 to flow therein. The far-side portion of the near-side shaft 60 is fixed to the near-side portion of the intermediate shaft 72.

The near-side shaft 60 should preferably be made of a relatively highly rigid material for producing an increased force with which the catheter 20 can be pushed into a living body lumen. For example, the relatively highly rigid material may be a metal such as stainless steel, stainless ductile alloy, Ni—Ti alloy, brass, aluminum, or the like, or a resin such as polyimide, vinyl chloride, polycarbonate, or the like.

As illustrated in FIG. 1, the hub 40 includes a port 41 in fluid communication with the near-side lumen 61 in the near-side shaft 60 for allowing the inflating fluid to flow through the port 41 into the near-side lumen 61 and out of the near-side lumen 61. The hub 40 is fixed to the near-side shaft 60 so that a fluid-tight seal is maintained between the hub 40 and the near-side shaft 60. When the inflating fluid flows through the port 41 into the near-side lumen 61, the inflating fluid flows through the near-side lumen 61 and the first lumen 71 into the balloon 30, inflating the balloon 30 radially outwardly.

The storage tubes 50 are tubular bodies into which the scoring wires 80 can be inserted. The number of storage tubes 50 is not limited to any particular number, but may be one or more. According to the present embodiment, the catheter 20 has three storage tubes 50. Each of the storage tubes 50 extends along an outer surface of the shaft 21 so that the storage tubes 50 extend in the longitudinal direction along the longitudinal extent of the shaft 21. Each of the storage tubes 50 has a first fixed portion 51, a second fixed portion 52, and a third fixed portion 53. As illustrated in FIGS. 2 and 3A, the first fixed portion 51 is fused to the balloon far-side fixed portion 32 that is fused to the inner tube 74. The first fixed portion 51 may be fixed to the balloon far-side fixed portion 32 by a process other than fusing, such as bonding, for example. The first fixed portion 51 may be fixed to a portion of the inner tube 74 that lies on a side farther than the balloon 30. In a case where the shaft 21 has a distal-end tip positioned on a side farther than the inner tube 74, the first fixed portion 51 may be fixed to the distal-end tip.

As illustrated in FIGS. 2 and 3C, the second fixed portion 52 is fixed to the outer tube 73 that is positioned on a side nearer than the balloon 30. According to the present embodiment, the second fixed portion 52 is fused to the outer tube 73. The second fixed portion 52 may be fixed to the outer tube 73 by a process other than fusing, such as bonding, for example. The second fixed portion 52 is disposed in a position that is relatively close to the balloon 30. Alternatively, the second fixed portion 52 may be fixed to a near-side portion of the balloon 30. The near-side portion of the balloon 30 may, for example, be the balloon near-side fixed portion 33 where the balloon 30 is fused to the outer tube 73. The portion of each of the storage tubes 50 between the first fixed portion 51 and the second fixed portion 52 is disposed on an outer surface of the balloon 30 and not fixed to the balloon 30. Therefore, the balloon 30 is pliable and easily becomes small in diameter. The portion of each of the storage tubes 50 between the first fixed portion 51 and the second fixed portion 52 may alternatively be fixed to the outer surface of the balloon 30.

As illustrated in FIGS. 2 and 3E, the third fixed portion 53 is disposed in a near-side portion of each of the storage tubes 50. The third fixed portion 53 is fixed to a portion of the shaft 21 that lies on a side nearer than the second fixed portion 52. According to the present embodiment, the portion of the shaft 21 to which the third fixed portion 53 is fixed is the intermediate shaft 72. Alternatively, the third fixed portion 53 may be fixed to the outer tube 73 or the near-side shaft 60. As illustrated in FIGS. 2 and 3D, the portion of each of the storage tubes 50 between the second fixed portion 52 and the third fixed portion 53 is not fixed to an outer surface side of the shaft 21. Therefore, the shaft 21 is pliable. Alternatively, the portion of each of the storage tubes 50 between the second fixed portion 52 and the third fixed portion 53 may be fixed to the outer surface of the shaft 21.

As illustrated in FIG. 2, a storage lumen 54 is located inside each of the storage tubes 50. Each storage lumen 54 is open at an insertion port 55 defined in a near-side portion of the storage tube 50 and is also open at a longitudinally extending opening portion 56 defined in a portion of the storage tube 50 that extends along the outer surface of the balloon 30, as illustrated in FIGS. 2 and 3B. The insertion port 55 is defined at a position where the scoring wire 80 can be inserted therethrough into the storage tube 50. The opening portion 56 acts as an area where the scoring wire 80 inserted in the storage tube 50 can project out of or be exposed outside of the storage tube 50. The opening portion 56 extends along the outer surface of the balloon 30 along the longitudinal axis of the shaft 21. The opening portion 56 provides fluid communication between the storage lumen 54 and an outer circumferential surface of the storage tube 50. The opening portion 56 is open radially outwardly of the shaft 21. Each of the storage tubes 50 is disposed between two adjacent flaps 34. The flexural rigidity of the portion of each of the storage tubes 50 along the outer surface of the balloon 30 is lower than the flexural rigidity of the balloon 30. Consequently, the storage tubes 50 do not impair the pliability of the balloon 30. Furthermore, the flexural rigidity of each of the storage tubes 50 is lower than the flexural rigidity of a scoring element 81, to be described later, of each of the scoring wires 80.

Each of the storage tubes 50 has a first stopper 58, a second stopper 59, and a third stopper 57. As illustrated in FIGS. 2 and 3A, the third stopper 57 restrains the scoring wire 80 stored in the storage lumen 54 from moving toward a far side. The third stopper 57 is provided by a closed end of the storage lumen 54 on the far side of the storage tube 50. The third stopper 57 is disposed in the first fixed portion 51. When the first fixed portion 51 is fused to the shaft 21, the third stopper 57 is created by eliminating or closing a space in the storage lumen 54. The position where the third stopper 57 is disposed is not limited to a position within the first fixed portion 51. Furthermore, the third stopper 57 may have a storage lumen 54 defined therein that is of a size capable of restraining the scoring wire 80 from moving toward a far side.

As illustrated in FIGS. 2, 3B through 3D, the second stopper 59 acts as a member for restraining the scoring wire 80 stored in the storage lumen 54 from rotating in the storage lumen 54. The second stopper 59 projects from an inner surface of the storage lumen 54 and is elongated or extends in the longitudinal directions of the storage tube 50. The second stopper 59 is disposed opposite the opening portion 56 in a cross section perpendicular to the longitudinal axis of the storage tube 50. The second stopper 59 can slidably enter a groove 85 (see FIG. 4A) defined in the scoring wire 80 as described later.

As illustrated in FIGS. 2 and 3E, the first stopper 58 acts as a member for restraining the scoring wire 80 stored in the storage lumen 54 from being dislodged from the storage lumen 54. The first stopper 58 is disposed at an angle that is different from the angle (see FIGS. 3B through 3D) at which the second stopper 59 is disposed in circumferential directions of the storage tube 50. That is, the first stopper 58 is disposed at a different circumferential position relative to the second stopper 59 as seen from the axial end. According to the present embodiment, the first stopper 58 projects from an inner surface of the storage lumen 54 at a position in the storage tube 50 that is spaced from the shaft 21. In the illustrated embodiment shown in FIG. 3(E) as one example, the first stopper 58 is located diametrically opposite the shaft 21 and projects toward the shaft 21. The first stopper 58 has a limiting surface 58A facing a far side and able to contact a stepped surface 84 of the scoring wire 80 as described later. The first stopper 58 should preferably be positioned in the vicinity of the insertion port 55. Alternatively, the first stopper 58 may not be included in the storage tube 50. Specifically, for example, the first stopper 58 may project from an outer surface of the outer tube 73, i.e., the shaft 21, positioned on a near side of the insertion port 55.

The outside diameter of the storage tube 50 is not limited to any particular outside diameters, but may be in the range from 2.0 to 0.05 mm, preferably in the range from 1.0 to 0.1 mm, and more preferably in the range from 1.0 to 0.15 mm. The inside diameter of the storage tube 50 is not limited to any particular inside diameter, but may be in the range from 1.5 to 0.03 mm, for example, preferably in the range from 0.8 to 0.08 mm, and more preferably in the range from 0.6 to 0.12 mm. The length of the storage tube 50 along the longitudinal axis is not limited to any particular lengths, but may be in the range from 10 to 400 mm, for example, preferably in the range from 100 to 350 mm, and more preferably in the range from 200 to 300 mm.

The material of the storage tubes 50 is not limited to any particular materials, though they may be made of any of the materials that are applicable to the outer tube 73, the inner tube 74, and the intermediate shaft 72. The material of the storage tubes 50 is softer than the material of the scoring element 81. Softness or hardness can be compared by way of Rockwell hardness, Brinell hardness, Vickers hardness, Shore hardness, or the like, for example.

The portion of each of the storage tubes 50 between the first fixed portion 51 and the second fixed portion 52 may be fixed to the outer surface of the balloon 30.

Next, the structure of each of the scoring wires 80 will be described below. As illustrated in FIGS. 1, 2, 4A, and 4B, the scoring wire 80 has a cross-sectional shape having a size configured to be inserted into the storage lumens 54 in the storage tubes 50. The scoring wires 80 should preferably be equal in number to the number of storage tubes 50. The scoring wire 80 has a scoring element 81 and a manipulating wire 82. The scoring element 81 is a member that can be positioned radially outwardly of the balloon 30. The scoring element 81 has a cross-sectional shape that is constant along the longitudinal axis of the scoring element 81.

The scoring element 81 has a cross-sectional shape perpendicular to the longitudinal axis of the scoring element 81, and the cross-sectional shape should preferably be a shape tapered radially outwardly of the shaft 21, for example. The cross-sectional shape of the scoring element 81, which is perpendicular to the longitudinal axis of the scoring element 81, is a substantially triangular shape, for example. One of the corners of the triangular shape acts as an edge 83 of the scoring element 81 for intensifying forces on a region contacted by the scoring element 81 to fracture the region. The cross-sectional shape of the scoring element 81 is not limited to any particular cross-sectional shapes as long as it is able to fracture lesion areas and biotissues, but may be of a polygonal cross-sectional shape, a circular cross-sectional shape, or other cross-sectional shapes. The scoring element 81 has a groove 85 defined in a surface thereof that is opposite the edge 83, the second stopper 59 is configured to slidably enter the groove 85. The groove 85 extends along the longitudinal axis of the scoring element 81.

The scoring element 81 can move with the storage lumen 54 to a position radially outward of the balloon 30 (see FIGS. 6A and 6B). The length of the scoring element 81 along the longitudinal axis thereof is not limited to any particular lengths, but should be substantially identical to the length of the opening portion 56 in the storage tube 50. The scoring element 81 may not have the groove 85, but may have a protrusion, not illustrated, extending along the longitudinal axis of the scoring element 81. According to such a modification, the second stopper 59 of the storage tube 50 may not be a projecting member, but may be a recess extending along the longitudinal axis of the scoring element 81 for receiving the protrusion of the scoring element 81 that has slidably entered the recess.

The manipulating wire 82 acts as a member that the surgeon manipulates to move the scoring element 81 in the storage lumen 54. The manipulating wire 82 is a wire extending from the scoring element 81 toward a near side. The manipulating wire 82 has a cross-sectional shape that is substantially constant along the longitudinal axis of the manipulating wire 82. The cross-sectional shape of the manipulating wire 82 is not limited to any particular cross-sectional shapes, but may be circular, for example. The outside diameter of the manipulating wire 82 is smaller than the inside diameter of the storage tube 50. While the scoring element 81 is stored in the storage lumen 54, the manipulating wire 82 should preferably, but not necessarily, have a near-side end positioned in the vicinity of the hub 40 so that the surgeon can easily manipulate the manipulating wire 82. The manipulating wire 82 should preferably, but not necessarily, be integral with the scoring element 81. The scoring wire 80 should preferably be longer than the storage tube 50 and as long as the shaft 21, though the scoring wire 80 may be shorter or longer than the shaft 21. The scoring element 81 has a stepped surface 84 facing a near side in a region thereof connected to the manipulating wire 82. The stepped surface 84 acts as an area for contacting the limiting surface 58A of the first stopper 58.

The outside diameter of the scoring wire 80, or the outside diameter of a circle circumscribing the cross-sectional shape of the scoring wire 80 if it is not circular, is not limited to any particular outside diameters, but may be in the range from 1.0 to 0.01 mm, for example, preferably in the range from 0.8 to 0.05 mm, and more preferably in the range from 0.4 to 0.1 mm. The length of the scoring wire 80 along the longitudinal axis of the scoring wire 80 is not limited to any particular lengths, but may be in the range from 200 to 2500 mm, for example, preferably in the range from 500 to 2000 mm, and more preferably in the range from 1000 to 1800 mm. The length of the scoring element 81 along the longitudinal axis is not limited to any particular lengths, but may be in the range from 20 to 300 mm, for example, preferably in the range from 10 to 100 mm, and more preferably in the range from 5 to 50 mm.

The scoring wire 80 is made of a metal (including an alloy), a resin, or the like. The metal may be, for example, stainless steel, aluminum, aluminum alloy, titanium, titanium alloy, copper, copper-based alloy, tantalum, or cobalt alloy. The resin may be, for example, polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate, polyethylene naphthalate, or the like, butadiene-styrene copolymer, or polyamide (e.g., nylon 6, nylon 6.6, nylon 6.10, nylon 12).

The scoring wire 80 may be made of a shape memory alloy to which a shape memory effect and superelasticity are imparted by a heat treatment, for example. Ni—Ti alloy, Cu—Al—Ni alloy, Cu—Zn—Al alloy, or the like may be used as the shape memory effect.

Operation and advantages of the scoring device 10 according to the present embodiment described above as well as a method of using the scoring device 10 will be described below.

First, as illustrated in FIG. 3E, the surgeon starts a surgical procedure by inserting the scoring wires 80 respectively into the storage lumens 54 through the insertion ports 55 of the respective storage tubes 50. At this time, the surgeon keeps the grooves 85 in the scoring elements 81 in positional alignment with the respective first stoppers 58 projecting into the insertion ports 55. Since the third fixed portions 53 of the storage tubes 50 are fixed to the shaft 21, the surgeon can easily insert the scoring wires 80 into the respective insertion ports 55. Then, the surgeon moves the manipulating wires 82 in a far-side direction. The scoring elements 81 are now inserted into the respective storage lumens 54. At this time, the first stoppers 58 slide in the respective grooves 85 in the scoring elements 81. Therefore, the scoring elements 81 are not restrained from moving by the first stoppers 58.

After the entire scoring elements 81 have reached the far side of the first stoppers 58, the surgeon turns the manipulating wires 82 about their longitudinal axes through approximately 180°, as illustrated in FIG. 5. The angle of approximately 180° through which the manipulating wires 82 are turned is the same as the angle through which the second stoppers 59 are angularly spaced (circumferentially spaced) from the first stoppers 58 in a cross section perpendicular to the longitudinal axis of the storage tubes 50. The grooves 85 are now positioned on a near side of the second stoppers 59. When the scoring wires 80 are then moved toward a near side, the stepped surfaces 84 of the scoring elements 81 are brought into contact with the limiting surfaces 58A of the first stoppers 58. Consequently, the scoring elements 81 are prevented from being dislodged from the storage tubes 50. The operability of the scoring device 10 thus increases. Since the manipulating wires 82 are thinner than the scoring elements 81, the manipulating wires 82 do not contact the first stoppers 58 when the scoring wires 80 are turned about their longitudinal axes. Alternatively, the first stoppers 58 may contact the manipulating wires 82 to an extent that does not refrain the manipulating wires 82 from moving. The second stoppers 59 are not disposed in a range where the scoring elements 81 are positioned after the entire scoring elements 81 have reached the far side of the first stoppers 58, so that the scoring elements 81 can be turned about their longitudinal axes.

Next, the surgeon inserts the scoring device 10 into a blood vessel through a guiding catheter or a sheath that has been percutaneously inserted into the blood vessel. Then, under fluoroscopy, the surgeon places the balloon 30 in a lesion area in the blood vessel. At this time, the storage tubes 50 are not positioned radially outwardly of the balloon 30. Moreover, the portions of the storage tubes 50 between the first fixed portion 51 and the second fixed portion 52 are not fixed to the balloon 30. Therefore, the balloon 30 is pliably bendable and is of a small diameter. As a result, the balloon 30 can easily move in the blood vessel that may be tortuous and can easily enter the lesion area that may be small.

Then, the surgeon lets an inflating fluid flow into the catheter 20 through the port 41 of the hub 40. The inflating fluid flows through the near-side lumen 61 and the first lumen 71 into the balloon 30. The inflating fluid introduced into the balloon 30 inflates the balloon 30 radially outwardly, possibly dilating the lesion area. If the lesion area is dilated to a desired size, then the dilating of the lesion area is completed. Since the scoring elements 81 for scoring lesion areas are not used at this time, the blood vessel into which the scoring device 10 is inserted remains highly safe.

On the other hand, if the lesion area cannot be dilated or sufficiently dilated by the balloon 30, then the surgeon discharges the inflating fluid from the balloon 30, allowing the balloon 30 to deflate. Next, the surgeon pushes the manipulating wires 32 to move toward the far side. At this time, the second stoppers 59 have entered the grooves 85 in the scoring elements 81. Therefore, the scoring elements 81 are prevented from being turned about their longitudinal axes by the second stoppers 59.

As illustrated in FIG. 6A, when the scoring elements 81 reach the position where the opening portions 56 are defined in the storage tubes 50, the edges 83 face the respective opening portions 56. As the scoring elements 81 are restrained from turning by the second stoppers 59, the edges 83 face the opening portions 56 reliably. When the surgeon excessively pushes in the scoring wires 80, the far-side ends of the scoring wires 80 abut against the third stoppers 57 that are positioned in the far-side portions of the storage lumens 54 as illustrated in FIG. 2. Therefore, the scoring wires 80 do not project toward the far side beyond the storage lumens 54. The scoring wires 80 that have thin far-side ends are thus refrained from scratching a biotissue.

Next, the surgeon lets the inflating fluid flow into the catheter 20 through the port 41 of the hub 40. The inflating fluid flows through the near-side lumen 61 and the first lumen 71 into the balloon 30. As illustrated in FIG. 6B, the balloon 30 is inflated radially outwardly, pressing the scoring elements 81 against a lesion area L. The storage tubes 50 are deformed into a flattened shape, forcing the edges 83 of the scoring elements 81 to protrude through the opening portions 56 into contact with the lesion area L. The edges 83 apply intensified forces to a lesion area L, scoring or fracturing the lesion area L. When the inflating fluid further inflates the balloon 30, the blood vessel spreads from the fractured regions of the lesion area L and is dilated. The storage tubes 50 may not be deformed into a flattened shape, but may be deformed in a manner to widen the opening portions 56.

Thereafter, the surgeon discharges the inflating fluid from the balloon 30, allowing the balloon 30 to deflate. The storage tubes 50 now return to their original shape or nearly original shape, housing the edges 83 of the scoring elements 81 therein. The balloon 30 may be inflated repeatedly a plurality of times. Then, the surgeon removes the scoring device 10 from the blood vessel, whereupon the surgical procedure is completed.

As described above, the scoring device 10 according to the present embodiment includes an elongate shaft 21, a balloon 30 disposed on a far side of the shaft 21 and inflatable radially outwardly of the shaft 21 by a fluid flowing into the balloon 30, at least one storage tube 50 disposed along an outer surface of the balloon 30 and having a storage lumen 54 defined therein, and an elongate scoring wire 80 storable in the storage tube 50 and made of a harder material than the balloon 30, the storage tube 50 being fixed to the balloon 30 or the shaft 21 and having an opening portion 56 defined therein that provides fluid communication between outer and inner circumferential surfaces of the storage tube 50 along the storage lumen 54 when the balloon 30 is inflated, and the scoring wire 80 being movable in the storage lumen 54 along a longitudinal axis of the storage tube 50.

The scoring device 10 thus constructed can be brought into a state in which the scoring wire 80 is not disposed in at least a portion of the storage tube 50 along the outer surface of the balloon 30. The balloon 30 on which the scoring wire 80 is not disposed is pliably bendable and tends to be small in diameter. Therefore, the scoring device 10 has an improved ability to pass through a living body lumen to a lesion area L and to track a guide wire. Depending on the number of scoring wires 80 inserted in respective storage tubes 50 and the rigidity of selected scoring wires 80, the pushability of the scoring device 10 can be adjusted.

The storage tube 50 has a lower flexural rigidity than the scoring wire 80. The storage tube 50 with no scoring wire 80 inserted therein does not impair the pliability of the balloon 30. Therefore, the balloon 30 is pliably bendable and tends to be small in diameter. Consequently, the ability of the scoring device 10 to pass through a living body lumen to a lesion area L and to track a guide wire is increased.

The storage tube 50 has a first fixed portion 51 fixed to a far-side portion of the balloon 30 or a portion of the shaft 21 that lies on a side farther than the balloon 30. Accordingly, the pliability of a substantially central inflatable region of the balloon 30 is not impaired by the first fixed portion 51. Therefore, the balloon 30 is pliably bendable and tends to be small in diameter. Consequently, the ability of the scoring device 10 to pass through a living body lumen to a lesion area L and to track a guide wire is increased.

The storage tube 50 extends toward a near side from the balloon 30 and has an insertion port 55 defined in a near-side portion thereof, with the storage lumen 54 being open through the insertion port 55. The insertion port 55 is thus positioned near the hands of the surgeon, allowing the surgeon to insert the scoring wire 80 into the insertion port 55 with ease. The scoring device 10 thus has its operability increased.

The storage tube 50 has a second fixed portion 52 on a near-side portion of the balloon 30 or a portion of the shaft 21 that lies on a side nearer than the balloon 30. Therefore, the storage tube 50 is kept in an appropriate position, not too far from the balloon 30. The storage tube 50 is thus refrained from being entangled with other instruments, a lesion area L, and so on. As the storage tube 50 is kept in an appropriate position, the scoring wire 80 that projects from the storage tube 50 can contact a biotissue at an appropriate position.

The storage tube 50 has a third fixed portion 53 fixed to the shaft 21 at a position closer to the insertion port 55 than the position where the second fixed portion 52 is disposed. The fixed portion 52 is thus less liable to move with respect to the shaft 21. Therefore, the surgeon finds it easy to insert the scoring wire 80 into the insertion port 55.

The storage tube 50 has a lower flexural rigidity than the balloon 30. The storage tube 50 is thus pliably deformable easily in tracking the balloon 30. Therefore, the ability of the scoring device 10 to pass through a living body lumen to a lesion area L and to track a guide wire is increased.

The opening portion 56 is open radially outwardly of the shaft 21. A portion of the scoring wire 80 in the storage lumen 54 can be exposed radially outwardly through the opening portion 56. When the balloon 30 is inflated, the scoring wire 80 is pressed through the opening portion 56 against a lesion area L, effectively spreading the lesion area L.

The scoring wire 80 has a scoring element 81 including an edge 83 that is defined as a corner in a cross section perpendicular to the longitudinal axis of the scoring wire 80 and a manipulating wire 82 extending toward a near side from the scoring element 81. The surgeon can grip the manipulating wire 82, rather than the scoring element 81 including the edge 83, to manipulate the scoring device 10. The scoring device 10 thus has its operability as well as safety increased.

The scoring wire 80 has a stepped surface 84 facing a near side, on a far side from a near-side end thereof. The storage tube 50 or the shaft 21 has a first stopper 58 disposed near the insertion port 55 and having a limiting surface 58A facing a near side and able to contact the stepped surface 84. When the scoring wire 80 stored in the storage lumen 54 moves toward a near side, the stepped surface 84 is brought into contact with the limiting surface 58A. The scoring wire 80 is thus refrained from being unintentionally dislodged from the storage tube 50. The operability of the scoring device 10 is thus increased.

The scoring wire 80 has a groove 85 or a protrusion extending along the longitudinal axis thereof, and the storage tube 50 has a second stopper 59 as a projecting member extending along the longitudinal axis thereof and able to enter the groove 85 or a recess extending along the longitudinal axis thereof and able to receive the projecting member entering the recess. The scoring wire 80 is thus restrained from turning in the storage lumen 54 by the second stopper 59. Therefore, the scoring wire 80 can have the edge 83 pointed in an appropriate direction.

The balloon 30 has a plurality of pleats 34 projecting radially outwardly and coiled circumferentially around the shaft 21, and the storage tube 50 is disposed between adjacent ones of the pleats 34. The storage tube 50 is efficiently placed between the coiled pleats 34. Therefore, the balloon 30 can be folded to a small size and tends to be small in diameter. Consequently, the ability of the scoring device 10 to pass through a living body lumen to a lesion area L and to track a guide wire is increased.

The storage tube 50 has a third stopper 57 on a far-side portion thereof, for closing the storage lumen 54 or restraining the scoring wire 80 in the storage lumen 54 from moving toward a far side. The scoring wire 80 in the storage lumen 54 is thus restrained from projecting toward a far side beyond the storage tube 50 by the third stopper 57. The scoring wire 80 that has a thin far-side end is thus refrained from contacting and hence scratching a biotissue, thus resulting in increased safety of the scoring device 10.

The storage tube 50 is separate from an inflatable portion of the balloon 30. In other words, the storage tube 50 is not fixed to an inflatable portion of the balloon 30. Therefore, the balloon 30 is pliably bendable and tends to be small in diameter. Consequently, the ability of the scoring device 10 to pass through a living body lumen to a lesion area L and to track a guide wire is increased. The inflatable portion of the balloon 30 is a portion into which a fluid can flow, and does not include portions fixed to the shaft 21, i.e., a balloon far-side fixed portion 32 and a balloon near-side fixed portion 33.

The present disclosure also covers a treatment method for dilating a lesion area L in a living body lumen. The treatment method includes inserting a balloon 30 with at least one storage tube 50 disposed on an outer surface thereof into a living body lumen until the balloon 30 reaches a lesion area L therein, inflating the balloon 30, deflating the balloon 30, placing an elongate scoring wire 80 made of a harder material than the balloon 30 in a portion of the storage tube 50 along the outer surface of the balloon 30, inflating the balloon 30 to apply a force to the scoring wire 80 to fracture at least a portion of the lesion area L, and causing the balloon 30 to dilate the lesion area L.

The treatment method arranged as described above is able to try to dilate a lesion area L using the balloon 30 that is pliable and small in diameter with no scoring wire 80 disposed thereon. In a case where the lesion area L cannot be dilated by the balloon 30 alone, the treatment method uses the scoring wire 80 to fracture the lesion area L while dilating the lesion area L.

The present disclosure is not limited to the embodiment described above, but many changes and modifications can be made in the embodiment by those skilled in the art within the scope of the technical concept of the present disclosure. For example, the scoring device 10 that is illustrated as being of the rapid-exchange type may be of the over-the-wire type.

The living body lumen into which the scoring device 10 can be inserted is not limited to a blood vessel, but may be a bile duct, a windpipe, an esophagus, a urethra, or any of other organs.

Figure 7A:
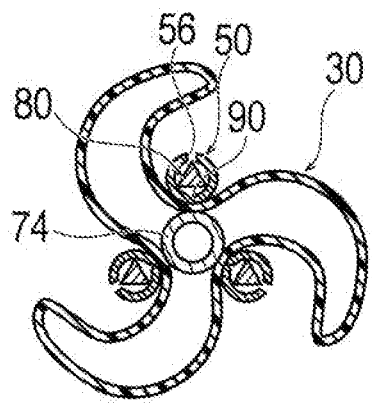
FIG. 7A is a transverse cross-sectional view illustrating a scoring device according to a first modification.

FIG. 7A illustrates a scoring device according to a first modification. As illustrated in FIG. 7A, the scoring device according to the first modification includes a storage tube 50 having a portion positioned opposite an opening portion 56 in a cross section perpendicular to the longitudinal axis of the storage tube 50, for inducing a pliable deformation of the storage tube 50. The portion of the storage tube 50 for inducing a pliable deformation thereof acts as a deformation inducing portion 90 for making an opening portion 56 in the storage tube 50 easy to open. The deformation inducing portion 90 is a thinned wall portion disposed substantially opposite the opening portion 56 in the cross section perpendicular to the longitudinal axis of the storage tube 50. According to the first modification, the deformation inducing portion 90 is formed as a V-shaped recess. Under a force applied from an inflating balloon 30, the storage tube 50 is greatly deformed at the deformation inducing portion 90, widening the opening portion 56. Therefore, a scoring wire 80 stored in the storage tube 50 can easily project through the opening portion 56 that is widened by the inflating balloon 30 into contact with a lesion area L.

Figure 7B:
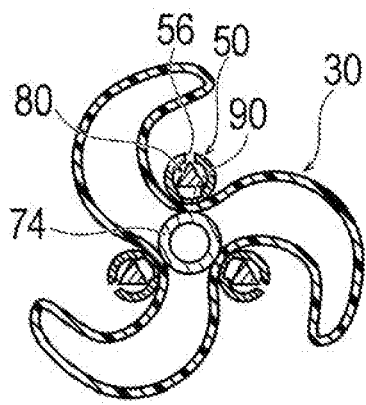
FIG. 7B is a transverse cross-sectional view illustrating a scoring device according to a second modification.

FIG. 7B illustrates a scoring device according to a second modification. As illustrated in FIG. 7B, according to the second modification, a deformation inducing portion 90 is a thinned wall portion having a certain width in the circumferential directions of the storage tube 50. The deformation inducing portion 90 may not be a thinned wall portion, but may be formed otherwise as long as it can make an opening portion 56 easy to open. For example, the deformation inducing portion 90 may be a member more fragile than portions adjacent thereto, may include a plurality of short slits or small holes arranged in an array, or a blind notch.

Figure 8A:
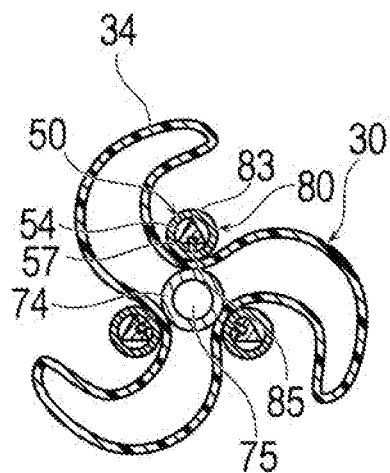
FIG. 8A is a transverse cross-sectional view illustrating a scoring device according to a third modification before a balloon is inflated.
Figure 8B:
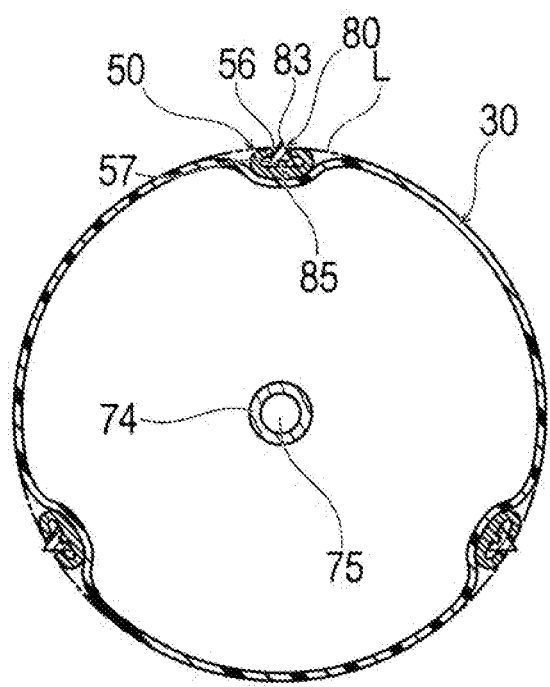
FIG. 8B is a transverse cross-sectional view illustrating the scoring device according to the third modification with the balloon inflated.

FIG. 8A illustrates a scoring device according to a third modification. As illustrated in FIG. 8A, a storage tube 50 has an opening portion 56 defined therein that is positioned in a portion other than the portion of the storage tube 50 that extends along the outer surface of a balloon 30. In other words, the opening portion 56 in the storage tube 50 is open when the balloon 30 is inflated, and remains closed before the balloon 30 is inflated. The storage tube 50 thus stores a scoring wire 80 in a storage lumen 54 while preventing the scoring wire 80 from unintentionally projecting from the storage lumen 54. The scoring wire 80 that is thin is thus restrained from contacting a biotissue other than a lesion area L, resulting in increased safety of the scoring device 10. The opening portion 56 that remains closed before the balloon 30 is inflated may be defined in a portion more fragile than portions adjacent thereto so that it can easily be fractured. For example, the opening portion 56 may be defined in a thinned wall portion, may include a hole closed by bonding or fusing with a weak joining force, a hole closed by a member more fragile than portions adjacent thereto, a plurality of short slits or small holes arranged in an array, or a blind notch. When the balloon 30 is inflated, an edge 83 of a scoring element 81 that is pushed by the inflating balloon 30 cuts open the opening portion 56 in the storage tube 50 and contacts a lesion area L, as illustrated in FIG. 8B. Therefore, the edge 83 can projects from the opening portion 56 that has been cut open by itself.

FIGS. 9A and 9B illustrate a scoring device according to a fourth modification. As illustrated in FIGS. 9A and 9B, a storage tube 50 has a slit-like opening portion 91 defined therein that extends from an opening portion 56 and an insertion port 55. The slit-like opening portion 91 extends radially from an inner circumferential surface of the storage tube 50 to an outer circumferential surface of the storage tube 50. The slit-like opening portion 91 is narrower than the opening portion 56 in the circumferential directions of the storage tube 50. Therefore, the storage tube 50 with the slit-like opening portion 91 can retain a scoring wire 80 well therein. The slit-like opening portion 91 may be defined in the storage tube 50 only in the vicinity of the insertion port 55 and may not be defined in the vicinity of the opening portion 56. A first stopper 58 is disposed in the storage tube 50 near the insertion port 55 and has a size for preventing a scoring element 81 from being dislodged from the storage tube 50. For inserting the scoring wire 80 through the insertion port 55 into a storage lumen 54, the surgeon spreads the slit-like opening portion 91, widening the insertion port 55, and inserts the scoring wire 80 through the insertion port 55 into the storage lumen 54, as illustrated in FIG. 10A. When the entire scoring element 81 has reached the far side of the first stopper 58, the slit-like opening portion 91 is closed, storing the scoring element 81 in the storage lumen 54, as illustrated in FIG. 10B. When the scoring wire 80 then moves to a near side, a stepped surface 84 of the scoring element 81 is brought into contact with the first stopper 58. Therefore, the scoring element 81 is restrained from being dislodged from the storage tube 50, thereby increasing the operability of the scoring device 10.

The detailed description above describes embodiments of scoring devices and treatment methods representing examples of the inventive scoring devices and treatment methods disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method comprising:
   inserting a balloon into a living body lumen until the balloon reaches a lesion area in the living body lumen, the balloon including at least one storage tube on an outer surface of the balloon;
   inflating the balloon;
   deflating the balloon;
   placing an elongate scoring wire made of a material that is harder than the balloon in a portion of the storage tube that is on the outer surface of the balloon;
   inflating the balloon to apply an outwardly directed force to the scoring wire to cause the scoring wire to score at least a portion of the lesion area; and
   dilating the lesion area with the inflated balloon.

2. The treatment method according to claim 1, wherein the inflating of the balloon to apply the outwardly directed force to the scoring wire outwardly moves the scoring wire so that a portion of the scoring wire extends outwardly beyond an outer periphery of the storage tube, the portion of the scoring wire being positioned inwardly of the outer periphery of the storage tube before the inflating of the balloon to apply the outwardly directed force to the scoring wire.

3. The treatment method according to claim 1, wherein the scoring wire includes a manipulating wire and a scoring element fixed at a far-side portion of the manipulating wire, the placing of the elongate scoring wire in the portion of the storage tube includes inserting a far-side portion of the scoring wire into an opening at a near-side of the storage tube, and moving the scoring wire in a far-side direction by pushing the manipulating wire to position the scoring element at a position in alignment with an opening portion in the storage tube, the inflating of the balloon to apply the outwardly directed force to the scoring wire causing the scoring element to pass through the opening portion of the storage tube and score at least the portion of the lesion area.

* * * * *